(12) United States Patent
Garcia-Rodenas et al.

(10) Patent No.: US 9,781,947 B2
(45) Date of Patent: *Oct. 10, 2017

(54) COMPOSITION FOR USE IN THE PROMOTION OF MAGNESIUM ABSORPTION AND/OR MAGNESIUM RETENTION

(71) Applicant: NESTEC S.A., Vevey (CH)

(72) Inventors: Clara Garcia-Rodenas, Forel (CH); Matthias Hoppler, Thalwil (CH); Elizabeth Offord Cavin, Montreux (CH)

(73) Assignee: Nestec S.A., Vevey (CH)

( * ) Notice: Subject to any disclaimer, the term of this patent is extended or adjusted under 35 U.S.C. 154(b) by 455 days.

This patent is subject to a terminal disclaimer.

(21) Appl. No.: 14/352,588

(22) PCT Filed: Oct. 15, 2012

(86) PCT No.: PCT/EP2012/070404
§ 371 (c)(1),
(2) Date: Apr. 17, 2014

(87) PCT Pub. No.: WO2013/057072
PCT Pub. Date: Apr. 25, 2013

(65) Prior Publication Data
US 2014/0255543 A1  Sep. 11, 2014

(30) Foreign Application Priority Data

Oct. 18, 2011 (EP) .................................. 11185610

(51) Int. Cl.
| | | |
|---|---|---|
| *C12Q 1/68* | (2006.01) | |
| *A23L 1/30* | (2006.01) | |
| *A61K 31/202* | (2006.01) | |
| *A61K 31/702* | (2006.01) | |
| *A61K 31/715* | (2006.01) | |
| *A61K 35/745* | (2015.01) | |
| *A61K 35/747* | (2015.01) | |
| *A23L 33/00* | (2016.01) | |
| *A23L 33/10* | (2016.01) | |
| *A23L 33/105* | (2016.01) | |
| *A23L 33/12* | (2016.01) | |
| *A23L 33/135* | (2016.01) | |
| *A23L 33/21* | (2016.01) | |
| *A61K 35/00* | (2006.01) | |

(52) U.S. Cl.
CPC .............. *A23L 1/30* (2013.01); *A23L 33/10* (2016.08); *A23L 33/105* (2016.08); *A23L 33/12* (2016.08); *A23L 33/135* (2016.08); *A23L 33/21* (2016.08); *A23L 33/40* (2016.08); *A61K 31/202* (2013.01); *A61K 31/702* (2013.01); *A61K 31/715* (2013.01); *A61K 35/745* (2013.01); *A61K 35/747* (2013.01); *A61K 2035/115* (2013.01)

(58) Field of Classification Search
None
See application file for complete search history.

(56) References Cited

U.S. PATENT DOCUMENTS

| | | | | |
|---|---|---|---|---|
| 5,906,982 A | * | 5/1999 | Prieto ...................... | A23C 9/203 426/601 |
| 5,939,394 A | * | 8/1999 | Fleming ............... | A61K 9/0019 514/23 |
| 2007/0098821 A1 | | 5/2007 | Johnson | |
| 2010/0278781 A1 | * | 11/2010 | Hougee ................ | A23L 1/3014 424/93.4 |
| 2011/0020304 A1 | * | 1/2011 | Sprenger ................ | A23L 33/21 424/93.45 |
| 2011/0256269 A1 | * | 10/2011 | Medo ....................... | A23C 3/02 426/72 |
| 2011/0300204 A1 | * | 12/2011 | Van Der Beek ........ | A23L 33/12 424/439 |
| 2012/0178674 A1 | * | 7/2012 | Stahl ....................... | A23L 33/10 514/5.5 |

FOREIGN PATENT DOCUMENTS

| | | |
|---|---|---|
| EP | 2455387 | 5/2012 |
| JP | 08283162 | 10/1996 |
| WO | 0239835 | 5/2002 |
| WO | 2007101675 | 9/2007 |
| WO | WO 2008/116892 A1 * | 10/2008 |
| WO | WO 2011/069987 A1 * | 6/2011 |
| WO | 2012170021 | 12/2012 |
| WO | WO 2012170021 A1 * | 12/2012 ........... A23C 9/1512 |

OTHER PUBLICATIONS

Perez-Conesa et al. J. Sci. Food Agric. (2007) 87: 1059-1068.*
Stutte et al. Eur. J. Pediatrics (2009) 168: 1497-1503.*
Picaud et al. J. Pediatrics (20018) 153: 616-621).*
Ballow et al. Pediatric Research (1986) 20(9): 899-904.*
Picaud et al. J. Pediatrics (2008) 153: 616-621 this is a correction for the reference which was sited in the PTO-892 for the Office action mailed Oct. 19, 2016.*
International Search Report corresponding to related International Patent Application No. PCT/EP2012/070404 mailed Dec. 3, 2012.
International Written Opinion corresponding to related International Patent Application No. PCT/EP2012/070404 mailed Dec. 3, 2012.
Coudray et al. "Effects of Dietary Fibers on Magnesium Absorption in Animals and Humans" J. Nutr., 2003, vol. 133, pp. 1-4.

(Continued)

*Primary Examiner* — Susan Hanley
(74) *Attorney, Agent, or Firm* — K&L Gates LLP

(57) ABSTRACT

The invention discloses a composition comprising a mixture of oligosaccharides, said mixture containing at least one N-acetylated oligosaccharide, at least one sialylated oligosaccharide and at least one neutral oligosaccharide, for use in the promotion magnesium absorption and/or magnesium retention. The composition preferably further comprises at least one long chain polyunsaturated fatty acid and/or at least one probiotic. This composition is particularly adapted for use in infants notably preterm infants.

9 Claims, 1 Drawing Sheet

(56) References Cited

OTHER PUBLICATIONS

Rodrigues Lobo et al. "Effects of dietary lipid composition and inulin-type fructans on mineral bioavailability in growing rats" Nutrition, 2009, vol. 25, pp. 216-225.

Bohn "Dietary Factors Influencing Magnesium Absorption in Humans" Current Nutrition & Food Science, 2008, vol. 4, No. 1, pp. 1-20.

* cited by examiner

COMPOSITION FOR USE IN THE PROMOTION OF MAGNESIUM ABSORPTION AND/OR MAGNESIUM RETENTION

CROSS REFERENCE TO RELATED APPLICATIONS

The present application is a National Stage of International Application No. PCT/EP2012/070404, filed on Oct. 15, 2012, which claims priority to European Patent Application No. 11185610.0, filed Oct. 18, 2011, the entire contents of which are being incorporated herein by reference.

FIELD OF THE INVENTION

This invention relates to a composition for use in the promotion of magnesium absorption and/or magnesium retention. This composition is for use in mammals, preferably in humans, more preferably in infants.

BACKGROUND OF THE INVENTION

Magnesium (Mg) is the second-most abundant intracellular cation and, overall, the fourth-most abundant cation. Almost all enzymatic processes using phosphorus as an energy source require magnesium for activation. Magnesium is involved in nearly every aspect of biochemical metabolism (eg, DNA and protein synthesis, glycolysis, oxidative phosphorylation). Almost all enzymes involved in phosphorus reactions (eg, adenosine triphosphatase [ATPase]) require magnesium for activation. Magnesium serves as a molecular stabilizer of RNA, DNA, and ribosomes. Because magnesium is bound to ATP inside the cell, shifts in intracellular magnesium concentration may help regulate cellular bioenergetics such as mitochondrial respiration.

The total body content of magnesium in adults is about 2,000 mEq or 24 g. Approximately 60% of total body magnesium is located in bone and the remainder is in the soft tissues. Serum concentration of magnesium typically ranges from 1.8-2.5 mEq/L. Approximately a third of this is protein-bound. The free (i.e. unbound) fraction of magnesium is considered as the active component.

Magnesium is primarily absorbed in the small intestine at a rate depending on the dietary intake, in the healthy individual. Absorption occurs primarily in the jejunum and ileum via ionic diffusion (passive) and at low luminal concentrations through active transport processes. The sigmoid colon also has some capacity for magnesium absorption. A minimal daily intake of 0.3 mEq/kg of body weight has been suggested to prevent deficiency. Infants and children tend to have higher daily requirements than adults.

The kidney is the major excretory organ for absorbed Mg. The average excretion of Mg in urine per day usually varies between 2 and 5 mmol.

Magnesium deficiency and hypomagnesemia are often asymptomatic. However, severe symptomatic hypomagnesemia may manifest clinically as tetany and generalized seizures. Early manifestations may include muscle cramps, nausea, vomiting, and lethargy.

Although no comprehensive studies have addressed the actual incidence of hypomagnesemia stratified by age group, neonates, in particular preterm infants are more predisposed to develop hypomagnesemia. As a matter of facts, prematurity is considered to be one of the major risk factors for Mg deficiency (Caddell J L. *Magnesium in perinatal care and infant health. Magnes Trace Elem* 1991; 10(2-4):229-50). Key reasons for the high risk of deficiency in preterm infants are the limited magnesium stores in the body and the high requirement for bone and intracellular magnesium inherent to the accelerated growth rate in these infants. Magnesium deficiency can increase the risk of severe neonatal complications such as intracranial haemorrhage, periventricular leukomalacia or bronchopulmonary dysplasia, as well as of life-long sequelae such as cerebral palsy and chronic lung disease (Caddell J L, Graziani L J, Wiswell T E et al. *The possible role of magnesium in protection of premature infants from neurological syndromes and visual impairments and a review of survival of magnesium-exposed premature infants. Magnes Res* 1999; 12(3):201-16; Caddell J L. *Evidence for magnesium deficiency in the pathogenesis of bronchopulmonary dysplasia (BPD). Magnes Res* 1996; 9(3):205-16.)

Thus, there is a need for a nutritional composition for use in the promotion of magnesium absorption and/or magnesium retention, in particular in infants and young children, preferably infants, who were born preterm or with low-birth weight (LBW) or experienced intra-uterine growth retardation (IUGR) or suffer from malabsorption, chronic diarrhea, short bowel syndrome and/or from growth stunting because of malnutrition, such as suboptimal intra-uterine nutrition, and/or disease.

Oligosaccharides, especially fructo-oligosaccharides and inulin, are known to promote magnesium absorption and/or retention in a dose-depended manner. Medium to high doses equivalent to more than 5% of dietary intake of oligosaccharides are often required to observe a positive effect. However, the gastrointestinal tolerance of these medium to high doses is often poor, and lead to abdominal distension and pain, flatulence and in some cases diarrhea. Therefore, there is a need for a new nutritional composition that can promote magnesium absorption and/or magnesium retention, at a low dose, compatible with the absence of gastrointestinal symptoms and with a good digestive tolerance. There is more generally a need for this nutritional intervention in young mammals, in particular infants and children, preferably infants, but also young pets.

There is a need for such intervention that induces the maintenance of an adequate magnesium level, by means of promoting absorption and/or retention, in humans and in animals, especially in young mammals.

SUMMARY OF THE INVENTION

The present inventors have found surprisingly that the administration of a mixture of specific oligosaccharides, optionally in combination with at least one long chain polyunsaturated fatty acid (LC-PUFA) and/or at least one probiotic, is particularly effective in the promotion of magnesium absorption and/or magnesium retention.

Accordingly, the present invention provides a composition comprising a mixture of oligosaccharides, said mixture containing at least one N-acetylated oligosaccharide, at least one sialylated oligosaccharide and at least one neutral oligosaccharide, in the promotion of magnesium absorption and/or magnesium retention.

The composition according to the invention is preferably a nutritional composition.

This composition preferably further comprises at least one LC-PUFA.

This composition preferably further comprises at least one probiotic.

The LC-PUFA, if present, is preferably chosen among arachidonic acid (ARA) and docosahexanoic acid (DHA), more preferably the LC-PUFA is a mixture of ARA and DHA.

The probiotic, if present, is preferably chosen among probiotic bacterial strains, more preferably the probiotic is a *lactobacillus* or a *bifidobacterium*. In a preferred embodiment, the probiotic is *Lactobacillus rhamnosus*, *Bifidobacterium lactis* and *Lactobacillus reuteri*. In an even more preferred embodiment, the probiotic is *Bifidobacterium lactis*.

The neutral oligosaccharide is preferably chosen among fructooligosaccharides (FOS) and galactooligosaccharides (GOS), preferably GOS.

In one embodiment the oligosaccharide mixture may be derived from animal milk, such as one or more of cow, goat, sheep or buffalo milk. For example, it was obtained by cow's milk fractionation and further enzymatic treatment.

In a second embodiment the oligosaccharide mixture may be prepared using enzymatic, chemo-enzymatic and/or chemical means.

In a third embodiment the oligosaccharide mixture may be prepared using yeast and/or bacterial fermentation technologies. For example, yeast and/or bacterial cells expressing suitable enzymes such as glycosidases and/or glycosyl-transferases upon genetic modification or not might be used to this end.

The composition of the invention is preferably used for infants who were born preterm or with low-birth weight (LBW) or experienced intra-uterine growth retardation (IUGR) or suffer from malabsorption, chronic diarrhea, short bowel syndrome and/or from growth stunting because of malnutrition, such as suboptimal intra-uterine nutrition, and/or disease.

DETAILED DESCRIPTION OF THE INVENTION

As used herein, the following terms have the following meanings.

The term "child" means a human between the stages of birth and puberty. An adult is a human older than a child.

The term "infant" means a child under the age of 12 months.

The term "preterm infant" (or "premature infant") means an infant born at least than 37 weeks gestational age.

The term "low birth weight infant" means an infant having a liveborn weight less than 2,500 g.

The term "young child" means a child aged between one and three years.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The term "preterm infant formula" means an infant formula intended for a preterm infant.

The term "human milk fortifier" means a supplement used to increase the calories, protein, minerals and vitamins in breast milk fed to preterm infants or infants with a low birth weight.

The term "follow-on formula" means a foodstuff intended for particular nutritional use by infants aged over four months and constituting the principal liquid element in the progressively diversified diet of this category of person.

The term "starter infant formula" means a foodstuff intended for particular nutritional use by infants during the first four to six months of life.

The term "baby food" means a foodstuff intended for particular nutritional use by infants during the first years of life.

The term "infant cereal composition" means a foodstuff intended for particular nutritional use by infants during the first years of life.

The term "growing-up milk" means a milk-based beverage adapted for the specific nutritional needs of young children.

The term "weaning period" means the period during which the mother's milk or the infant formula is partially or totally substituted by other food in the diet of an infant. The term "promotion of magnesium absorption and/or magnesium retention" means the support of magnesium absorption, or the support of magnesium retention, or both.

The term "nutritional composition" means a composition which nourishes a subject. This nutritional composition is usually to be taken orally, intragastrically, or intravenously, and it usually includes a lipid or fat source and a protein source.

The term "synthetic mixture" means a mixture obtained by chemical and/or biological means, which can be chemically identical to the mixture naturally occurring in mammalian milks.

The term "hypoallergenic composition" means a composition which is unlikely to cause allergic reactions.

The term "probiotic" means microbial cell preparations or components of microbial cells or microbial cell metabolites with a beneficial effect on the health or well-being of the host. (Salminen S, Ouwehand A. Benno Y. et al. *"Probiotics: how should they be defined" Trends Food Sci. Technol.* 1999:10 107-10).

The term "oligosaccharide" means a carbohydrate having a degree of polymerisation (DP) ranging from 2 to 20 inclusive but not including lactose.

The term "neutral oligosaccharide" means an oligosaccharide having no charge and no N-acetyl residue.

The term "sialylated oligosaccharide" means an oligosaccharide having a sialic acid (such as N-acetylneuraminic acid and/or N-glycolylneuraminic acid) residue.

The term "N-acetylated" oligosaccharide means an oligosaccharide having at least one hexose carrying an N-acetyl residue.

All percentages are by weight unless otherwise stated.

In one aspect, the invention provides a composition, comprising a oligosaccharide mixture, said mixture containing at least one N-acetylated oligosaccharide selected from the group comprising GalNAcα1,3Galβ1,4Glc (=3'GalNAc-lac=N-acetyl-galactosaminyl-lactose) and Galβ1,6GalNAcα1,3Galβ1,4Glc (=6'Gal-3GalNAc-lac=galactosyl-N-acetyl-galactosaminyl-lactose), Galβ1,4GlcNAcβ1,3Galβ1,4Glc (lacto-N-neotetraose or LNnT) and Galβ1,3GlcNAcβ1,3Galβ1,4Glc (lacto-N-tetraose or LNT), at least one sialylated oligosaccharide selected from the group comprising NeuAcα2,3Galβ1,4Glc (=3'-sialyllactose) and NeuAcα2,6Galβ1,4Glc (=6'-sialyllactose), and at least one neutral oligosaccharide selected form the group consisting of Galβ1,6Gal (=β1,6-digalactoside); Galβ1,6Galβ1,4Glc (=6'Gal-lac); Galβ1,6Galβ1,6Glc; Galβ1,3Galβ1,3Glc; Galβ1,3Galβ1,4Glc (=3'Gal-lac); Galβ1,6Galβ1,4Glc (=6',6-diGal-lac); Galβ1,6Galβ1,3Galβ1,4Glc (=6',3-diGal-lac); Galβ1,3Galβ1,6Galβ1,4Glc (=3',6-diGal-lac); Galβ1,3Galβ1,3Galβ1,4Glc (=3',3-diGal-lac); Galβ1,4Galβ1,4Glc (=4' Gal-lac); and Galβ1, 4Galβ1,4Galβ1,4Glc (=4',4-diGal-lac); and Fucα1,2Galβ1,
4Glc (=2' fucosyllactose or FL),
for use in the promotion of magnesium absorption and/or
magnesium retention.

Preferably, the composition further comprises at least one LC-PUFA.

Preferably, the composition further comprises at least one probiotic.

In a second aspect, the invention relates to a composition comprising:
 0.25-20 wt %, preferably 0.3-10 wt %, more preferably 0.3-5 wt % and even more preferably around 0.5 wt %, with respect to the total weight of the oligosaccharide mixture, of at least one N-acetylated oligosaccharide,
 0.5-30 wt %, preferably 0.75-15 wt %, more preferably 0.75-10 wt % and even more preferably around 1 wt %, with respect to the total weight of the oligosaccharide mixture, of at least one sialylated oligosaccharide, and
 50-99.3 wt %, preferably 20-80 wt %, more preferably 10-50 wt % and even more preferably around 50 wt %, with respect to the total weight of the oligosaccharide mixture, of at least one neutral oligosaccharide,
for use in the promotion of magnesium absorption and/or magnesium retention.

According to a preferred embodiment, the oligosaccharide mixture is present in an amount of 0.5-50%, more preferably 1-20%, even more preferably 2-8%, with respect with the total weight of the composition.

The oligosaccharide compounds are defined by their structures, where GalNAc is N-acetyl galactosamine, GlcNAc is N-acetyl glucosamine, Gal is galactose, NeuAc is N-acetyl neuraminic acid, Fuc is fucose and Glc is glucose.

The oligosaccharide mixture of the composition according to the invention can be the only source of oligosaccharide in the composition.

In a first embodiment, the neutral oligosaccharide is preferably chosen among FOS and GOS, preferably GOS such as the ones cited above.

In a second embodiment, independent or not from the first embodiment, the neutral oligosaccharide is preferably 2'-fucosyllactose (FL). In this case, FL is preferably included in the group of neutral oligosaccharides in the oligosaccharide mixture during its manufacturing.

The neutral oligosaccharide may be prepared as a mixture by purchasing and mixing the individual components. For example, synthesised galacto-oligosaccharides such as Galβ1,6Gal, Galβ1,6Galβ1,4Glc, Galβ1,6Galβ1,6Glc, Galβ1,3Galβ1,3Glc, Galβ1,3Galβ1,4Glc, Galβ1,6Galβ1,6Galβ1,4Glc, Galβ1,6Galβ1,3Galβ1,4Glc Galβ1,3Galβ1,6Galβ1,4Glc, Galβ1,3Galβ1,3Galβ1,4Glc, Galβ1,4Galβ1,4Glc and Galβ1,4Galβ1,4Galβ1,4Glc and mixtures thereof are commercially available under the trademarks Vivinal® from Friesland Campina, Netherlands, and Elix'or®. Other suppliers of oligosaccharides are Dextra Laboratories, Sigma-Aldrich Chemie GmbH and Kyowa Hakko Kogyo Co., Ltd. Alliteratively, specific glycosyltransferases and/or glycosidases, such as galactosyltransferases, and/or fucosyltransferases and/or galactosidases and/or fucosidases may be used to produce galacto-oligosaccharides and/or fucosylated oligosaccharides.

The fucosyllactose is a fucosylated oligosaccharide (that is to say an oligosaccharide having a fucose residue). This fucosylated oligosaccharide may be isolated by chromatography or filtration technology from a natural source such as animal milks. Alternatively, it may be produced by biotechnological means using specific fucosyltransferases and/or fucosidase either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

According to the invention, the sialylated oligosaccharide can be selected from the group comprising 3'-sialyllactose and 6'-sialyllactose. Preferably, the sialylated oligosaccharide comprises both 3'-sialyllactose and 6'-sialyllactose. In this embodiment, the ratio between 3'-sialyllactose and 6'-sialyllactose lies preferably in the range between 5:1 and 1:2.

The 3'- and 6'-forms of sialyllactose may be obtained by adding to the composition a natural source such as animal milk, or may be isolated by chromatographic or filtration technology from such natural source. Alternatively, they may be produced by biotechnological means using specific sialyltransferases or sialidases, neuraminidases, by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

The N-acetylated oligosaccharides may be obtained by adding to the composition a natural source such as animal milk. Alternatively, they may be prepared by the action of glucosaminidase and/or galactosaminidase on N-acetyl-glucose and/or N-acetyl galactose. Equally, N-acetyl-galactosyl transferases and/or N-acetyl-glycosyl transferases may be used for this purpose. The N-acetylated oligosaccharides may also be produced through the use of fermentation technology using respective enzymes (recombinant or natural) and/or microbial fermentation. In the latter case the microbes may either express their natural enzymes and substrates or may be engineered to produce respective substrates and enzymes. Single microbial cultures or mixed cultures may be used. N-acetylated oligosaccharide formation can be initiated by acceptor substrates starting from any degree of polymerisation (DP), from DP=1 onwards. Another option is the chemical conversion of keto-hexoses (e.g. fructose) either free or bound to an oligosaccharide (e.g. lactulose) into N-acetylhexosamine or an N-acetylhexosamine containing oligosaccharide as described in Wrodnigg, T. M.; Stutz, A. E. (1999) Angew. Chem. Int. Ed. 38:827-828.

LNnT and LNT may be synthesised by enzymatic transfer of saccharide units from donor moieties to acceptor moieties using glycosylhydrolases and/or glycosyltransferases as described for example in U.S. Pat. No. 5,288,637 and WO 96/10086. Alternatively, LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

Preferably the N-acetylated oligosaccharide is selected from the group comprising lacto-N-neotetraose (or LNnT) and lacto-N-tetraose (or LNT). Preferably LNnT and/or LNT are included in the group of sialylated oligosaccharides in the oligosaccharide mixture during its manufacturing.

Probiotic bacterial strain optionally present in the composition of the invention may be selected from any strain which satisfies the definition of a probiotic and has acceptable shelf-life for the composition in which it will be incorporated. For example, if the composition is incorporated into an infant formulae, said infant formulae is required to remain stable and effective for up to 12 months. The probiotic bacterial strain is preferably a *lactobacillus* or a *bifidobacterium*, and more preferably a *bifidobacterium*.

Examples of preferred *Lactobacillus* species are *Lactobacillus rhamnosus, Lactobacillus paracasei* and *Lactobacillus reuteri*. Particularly preferred strains are *Lactobacillus rhamnosus* ATCC 53103, *Lactobacillus rhamnosus* CGMCC 1.3724, and *Lactobacillus paracasei* CNCM I-2116. Even more preferably the probiotic is *Lactobacillus rhamnosus*, term which covers *Lactobacillus rhamnosus* ATCC 53103 and *Lactobacillus rhamnosus* CGMCC 1.3724.

*Lactobacillus rhamnosus* ATCC 53103 is available from Valio Oy of Finland under the trademark LGG.

Examples of preferred *Bifidobacterium* species include *Bifidobacterium lactis, Bifidobacterium longum, Bifidobacterium breve* and *Bifidobacterium infantis*, Particularly preferred strains are *Bifidobacterium lactis* CNCM I-3446 sold inter alia by the Christian Hansen company of Denmark under the trade mark Bb12, *Bifidobacterium longum* ATCC BAA-999 sold by Morinaga Milk Industry Co. Ltd. of Japan under the trade mark BB536, the strain of *Bifidobacterium breve* sold by Danisco under the trade mark Bb-03, the strain of *Bifidobacterium breve* sold by Morinaga under the trade mark M-16V, the strain of *Bifidobacterium infantis* sold by Procter & Gamble Co. under the trade mark Bifantis and the strain of *Bifidobacterium breve* sold by Institut Rosell (Lallemand) under the trade mark R0070.

According to the invention, the optional probiotic is chosen among probiotic bacterial strains, preferably the probiotic is a *lactobacillus* or a *bifidobacterium*, more preferably the probiotic is *Lactobacillus rhamnosus, Lactobacillus reuteri* and *Bifidobacterium lactis*, and even more preferably the probiotic is *Bifidobacterium lactis*.

The probiotic can be present in the composition in a wide range of percentages provided that the probiotic delivers the effect described. However, preferably, the probiotic is present in the composition in an amount equivalent to from 10e2 to 10e12 cfu (=colony forming unit) of probiotic bacterial strain, more preferably between 10e6 and 10e9 cfu, for each gram of the composition. This expression includes the possibilities that the bacteria are alive, inactivated or dead or even present as fragments such as DNA, cell wall materials, intracellular materials or bacteria metabolites. In other words, the quantity of bacteria which the composition contains is expressed in terms of colony forming ability of that quantity of bacteria if all the bacteria were live irrespective of whether they are, in fact, live, inactivated or dead, fragmented or a mixture of any or all of these states.

The composition optionally contains at least one LC-PUFA, which is usually a n-3 or a n-6 LC-PUFA. The n-3 LC-PUFA can be a C20 or a C22 n-3 fatty acid. The C20 or C22 n-3 LC-PUFA is preferably present in an amount of at least 0.1 wt % of all fatty acids in the composition. Preferably the n-3 LC-PUFA is docosahexanoic acid (DHA, C22: 6, n-3). The n-6 LC-PUFA can be a C20 or a C22 n-6 fatty acid. The C20 or C22 n-6 LC-PUFA is preferably present in an amount of at least 0.1 wt % of all fatty acids in the composition. Preferably the n-6 LC-PUFA is arachidonic acid (ARA, C20:4, n-6). The source of LC-PUFA may be, for example, egg lipids, fungal oil, low EPA fish oil or algal oil. The optional LC-PUFA of the composition of the invention may be provided in small amounts of oils containing high quantities of preformed arachidonic acid and docosahexanoic acid such as fish oils or microbial oils.

The composition according to the invention is preferably a nutritional composition, more preferably a synthetic nutritional composition. In this case, it can be a preterm infant formula, a human milk fortifier, a starter infant formula, a follow-on formula, a baby food formula, an infant cereal formula, a growing-up milk, a medical food product for clinical nutrition, or a supplement, typically to be used during hospital stay and/or to be used after hospital discharge. A supplement can be for a preterm infant or a child or an adult. Said composition is preferably a product for preterm feeding such as a preterm infant formula, a human milk fortifier, or a preterm infant supplement. According to an embodiment, the composition is preferably a preterm infant formula, a human milk fortifier, or a supplement. The composition according to the invention can also be products for children or adults such as yogurt or medical food, as well as pets' food.

According to a particularly preferred embodiment, the composition according to the invention is for use in infants and young children who who were born preterm or with low-birth weight (LBW) or experienced intra-uterine growth retardation (IUGR) or suffer from malabsorption, chronic diarrhea, short bowel syndrome and/or from growth stunting because of malnutrition, such as suboptimal intra-uterine nutrition, and/or disease.

The composition according to the invention can be for use before and/or during and/or after a weaning period.

The invention includes also the use of a composition according to the invention, as a synthetic nutritional agent, for the promotion of magnesium absorption and/or magnesium retention.

All the uses stated above are particularly intended for infants and young children, preferably infants, in case of humans. But these uses are also intended for young pets. The compositions and uses as per the present invention are particularly suited for infants and young children, preferably infants, who were born preterm or with low-birth weight (LBW) or experienced intra-uterine growth retardation (IUGR) or suffer from malabsorption, chronic diarrhea, short bowel syndrome and/or from growth stunting because of malnutrition, such as suboptimal intra-uterine nutrition, and/or disease.

Without wishing to be bound by theory, the inventors believe that the efficacy of the combination of oligosaccharide mixture in the composition described above for the promotion of magnesium absorption and/or magnesium retention, may be the result of the synergistic combination of immunity modulator effects. This is even more the case when probiotic and/or LC PUFA is (are) present, because then the synergistic combination is triggered by the probiotic bacterial strain and/or the LC-PUFA through their stimulation with the specific oligosaccharide mixture.

The oligosaccharide mixture, the optional LC-PUFA and the optional probiotic bacterial strain may be administered in the same composition or may be administered sequentially.

If the preterm and LBW infant group is to be addressed, the composition is preferably a nutritional composition, for example consumed in liquid form. It may be a nutritionally complete formula such as a (preterm) infant formula, a supplement, a human milk fortifier, a follow-on formula or a growing-up milk. Alternatively, for the group of young mammals, the composition may be a pets' food.

The composition according to the invention can also contain a protein source. The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions. The proteins can be at last partially hydrolysed in order to enhancement of oral tolerance to allergens, especially food allergens. In that case the composition is a hypoallergenic composition.

The composition according to the present invention can also contain a carbohydrate source in addition to the oligosaccharide mixture. This is particularly preferable in the case where the composition of the invention is an infant formula. In this case, any carbohydrate source conventionally found in infant formulae such as lactose, saccharose, maltodextrin, starch and mixtures thereof may be used although the preferred source of carbohydrates is lactose. In any case, the oligosaccharide mixture is preferably the single source of prebiotic in the composition according to the invention.

The composition according to the present invention can also contain a source of lipids including or not the optional LC-PUFA. This is particularly relevant if the nutritional composition of the invention is an infant formula. In this case, the lipid source may be any lipid or fat which is suitable for use in infant formulae. Preferred fat sources include palm oleic, high oleic sunflower oil and high oleic safflower oil, optionally enriched with at least one LC-PUFA, such as ARA and/or DHA. The essential fatty acids linoleic and α-linolenic acid may also be added. In the composition, the fat source (including the LC-PUFA) preferably has a ratio of n-6 to n-3 fatty acids of about 1:2 to about 10:1, preferably about 3:1 to about 8:1.

The composition of the invention can also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, gangliosides, polyamines, and the like.

The preparation of the composition according to the invention will now be described by way of example.

The formula may be prepared in any suitable manner. For example, it may be prepared by blending together a protein source, a carbohydrate source (different from the oligosaccharide mixture), and a fat source including the optional LC-PUFA in appropriate proportions. If used, the emulsifiers may be included at this point. The vitamins and minerals may be added at this point but are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture. The oligosaccharide mixture will be added at this stage if the final product is to have a liquid form. If the final product is to be a powder, the oligosaccharides may likewise be added at this stage if desired. The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

The homogenised mixture is transferred to a suitable drying apparatus such as a spray dryer or freeze dryer and converted to powder. The powder should have a moisture content of less than about 5% by weight. The oligosaccharide mixture may be added at this stage by dry-mixing along with the optional probiotic bacterial strain(s), or by blending them in a syrup form of crystals, along with the optional probiotic bacterial strain(s), and spray-dry (or freeze dry).

If a liquid composition is preferred, the homogenised mixture may be sterilised then aseptically filled into suitable containers or may be first filled into the containers and then retorted.

In another embodiment, the composition of the invention may be a supplement in an amount sufficient to achieve the desired effect in an individual. This form of administration is usually more suited to preterm or LBW or IUGR infants, older children and adults.

The amount of oligosaccharide mixture, optional LC-PUFA and optional probiotic bacterial strain to be included in the supplement will be selected according to the manner in which the supplement is to be administered.

The supplement may be in the form of powder, tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

The supplement can be added in a product acceptable to the consumer (who is a human or an animal), such as an ingestible carrier or support, respectively. Examples of such carriers or supports are a pharmaceutical or a food or a pet food composition. Non-limiting examples for such compositions are milk, yogurt, curd, cheese, fermented milks, milk based fermented products, fermented cereal based products, milk based powders, human milk, preterm formula, infant formula, oral supplement, and tube feeding.

Further, the supplement may contain an organic or inorganic carrier material suitable for enteral or parenteral administration as well as vitamins, minerals trace elements and other micronutrients in accordance with the recommendations of Government bodies such as the USRDA.

BRIEF DESCRIPTION OF THE DRAWINGS

The advantages, nature, and various additional features of the invention will appear more fully upon consideration of the illustrative experiment now to be described in detail in connection with accompanying drawings. In the drawings.

EXAMPLE

Figure 1:
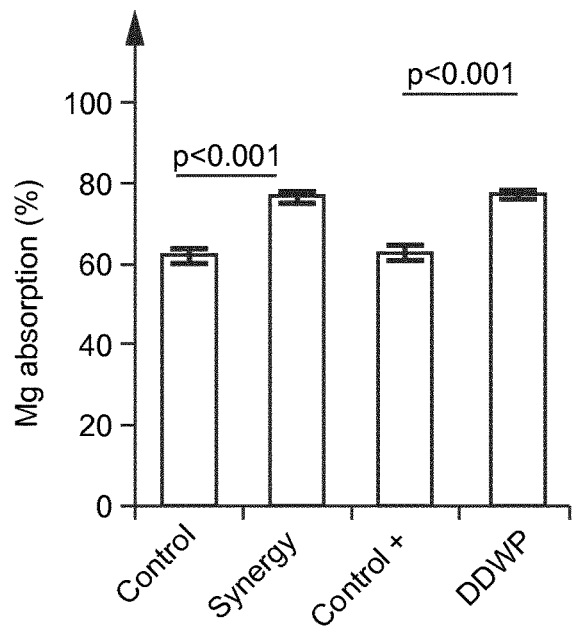
FIG. 1 is a bar graph plotting the results of the experiments, in terms of magnesium absorption (%).

Experiments were carried out with respect to the effect of the supplementation of a oligosaccharide mixture (demineralized, delactosed whey permeate or DDWP) which is a mixture of cow milk oligosaccharides (CMOS) enriched with galacto-oligosaccharides, on 7 weeks old rats.

Methodology

1. Experimental Protocol 40 male rats (Wistar), 7 weeks old were purchased from Charles River SA, France. Animals were acclimatised to the conditions of the animal facilities during 6 days upon arrival. During this time animals were kept individually in standard Macrolon cages and received the diet of group Control (see Tables 1-3). After the acclimatisation period, the animals were randomized into four groups according to their body weights and transferred during 7 days into cages with half wire bottom, to adapt them to the wire-bottom used later in the metabolic cages. From this moment until the end of the study, animals received the experimental diets according to the group (Control, Synergy, Control + and DDWP) they belong to (see Tables 1-3). During the last 7 days of the study, the animals were kept individually in metabolic cages in order to quantitatively collect urine and faecal samples.

2. Treatment and Diets

The following functional ingredients were used in the elaboration of the experimental diets:

CMOS (PTC Konolfingen, batch 24722): Demineralized, delactosed whey permeate spray-dry powder (Total oligosaccharide content: 1.3% on dry matter).

Vivinal® GOS (Friesland Foods Domo, NL): galacto-oligosaccharide syrup (Total oligosaccharide content: 58.1% on dry matter).

Synergy1® (Beneo-Orafty, BE). 1:1 Inulin and fructo-oligosaccharide blend powder (Total oligosaccharide content: 92% on dry matter).

The following dietary groups were studied:

Control. Fed with a semi-synthetic diet adapted for growth and based on AIN 93G. It was used as a control for the Synergy group.

Synergy. Fed with Control diet containing 10% (w/w) "Synergy1®"

Control +. Fed with Control diet supplemented with glucose, galactose, and lactose, as well as Na, Ca, Mg and P in similar concentrations as contributed by the DDWP ingredient. It was used as a control for the DDWP group.

DDWP. Fed with control diet containing 21.7% (w/w) CMOS and 8.6% (w/w) Vivinal® GOS, representing a concentration of 4% (w/w) oligosaccharides in the final diet.

The DDWP oligosaccharides are typically obtained according to the disclosures of WO2007/101675 or WO 2007/090894 and usually contains a mixture of about 30 wt % of GalNAcα1,3Galβ1,4Glc and Galβ1,6GalNAcα1,3Galβ1,4Glc; 50 wt % of Galβ1,6Galβ1,4Glc and Galβ1,3Galβ1,4Glc; 20 wt % of NeuAcα2,3Galβ1,4Glc and NeuAcα2,6Galβ1,4Glc.

Dietary intake was assessed daily during the last 14 days of the experiment. Urine and feces samples were quantitatively collected from day 16 till day 20.

The diets' compositions (having the same reference number as the corresponding diet groups) are given in the following Tables 1, 2 and 3.

TABLE 1

Composition of diets (g/100 g diet)

| | Control | Synergy | Control+ | DDWP |
|---|---|---|---|---|
| Cornstarch | 26.5 | 24.0 | 25.0 | 14.9 |
| Caseinate | 10.0 | 10.0 | 10.0 | 10.0 |
| Sucrose | 5.00 | 2.50 | 3.49 | 1.40 |
| Fat mix | 3.50 | 3.50 | 3.50 | 3.50 |
| Cellulose | 2.50 | 2.50 | 2.50 | 2.50 |
| Mineral Mix (AIN-93G-MX) | 1.75 | 1.75 | 1.75 | 1.75 |
| Vitamin Mix (AIN-93-VX) | 0.500 | 0.500 | 0.500 | 0.500 |
| L-Cystein | 0.150 | 0.150 | 0.150 | 0.150 |
| Choline bitartrate | 0.125 | 0.125 | 0.125 | 0.125 |
| Tert-butylhydroquinone | 0.001 | 0.001 | 0.001 | 0.001 |
| Millipore Water | 50.0 | 50.0 | 50.0 | 50.0 |
| Lactose | | | 2.73 | |
| Glucose | | | 0.081 | |
| Galactose | | | 0.054 | |
| Ca Phosphate | | | 0.062 | |
| Mg Oxide | | | 0.006 | |
| K Phosphate | | | 0.077 | |
| Synergy1 ® | | 5.00 | | |
| DDWP | | | | 10.9 |
| Vivinal ®-GOS | | | | 4.30 |
| Total (g) | 100 | 100 | 100 | 100 |

TABLE 2

Composition of the fat mix in diets (g/100 g fat mix)

|  | Control | Synergy | Control + | DDWP |
|---|---|---|---|---|
| Soybean oil | 15.32 | 15.32 | 15.32 | 15.32 |
| High oleic Sunflower oil | 3.98 | 3.98 | 3.98 | 3.98 |
| Cocoa butter | 34.36 | 34.36 | 34.36 | 34.36 |

TABLE 3

Concentration of mineral and macronutrients in diets

|  | Control | Synergy | Control + | DDWP |
|---|---|---|---|---|
| Calcium (mg/kg) | 5588 | 5495 | 5944 | 6167 |
| Magnesium (mg/kg) | 573 | 553 | 662 | 685 |
| Zinc (mg/Kg) | 30.0 | 28.4 | 30.4 | 30.0 |
| Ca/P ratio | 1.51 | 1.53 | 1.41 | 1.36 |
| Sodium (mg/kg) | 3925 | 4157 | 4218 | 4539 |
| Iron (mg/Kg) | 77.4 | 74.6 | 82.0 | 68.8 |
| Protein (N × 6.25, g/100 g) | 16.6 | 17.00 | 16.60 | 17.60 |
| Fat (g/100 g) | 6.48 | 7.12 | 6.62 | 7.20 |

3. Magnesium Parameters

Magnesium absorption efficiency (%), as shown in the bar graph of FIG. 1, for each one of the diet groups, was measured by ICP-OES analysis of balance of mineral concentrations in diet and feces.

Figure 2:
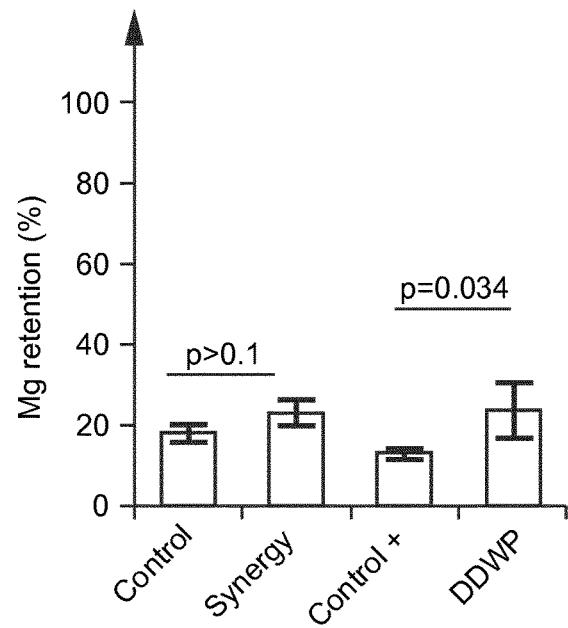
FIG. 2 is a bar graph plotting the results of the experiments, in terms of magnesium retention (%).

Magnesium retention (%), as shown in the bar graph of FIG. 2, for each one of the diet groups, was measured by ICP-OES analysis of balance of mineral concentrations in diet, faeces and urine.

"Synergy" is a mixture of oligosaccharides known to increase the digestive bioavailabilty of magnesium and other minerals (Coudray C, Tressol J C, Gueux E et al. *Effects of inulin-type fructans of different chain length and type of branching on intestinal absorption and balance of calcium and magnesium in rats*. Eur J Nutr 2003; 42(2):91-8; Lobo A R, Filho J M, Alvares E P et al. *Effects of dietary lipid composition and inulin-type fructans on mineral bioavailability in growing rats*. Nutrition 2009; 25(2):216-25). "Synergy" is to be compared to "control" because they have a similar composition in minerals and other nutrients. "Synergy" is known as improving magnesium absorption and/or retention in a dose-dependent manner.

The composition "Control +" is similar to the DDWP containing diet. Making these comparisons between each group of similar compositions, FIG. 1 shows that magnesium absorption is improved over the control diets ("Control" and "Control +") with both "Synergy" and DDWP-containing diet. FIG. 2 shows that magnesium retention is not significantly affected by "synergy", but it is improved with the diet DDWP according to the invention.

Those results are all the more interesting as the DDWP oligosaccharides are at a low dose (4%) in the diet, whereas Synergy is at a rather high dose (10%) in the diet, which digestive tolerance is expected to be low, especially in the infant population.

Thus, the nutritional compositions according to the invention showed an effect in the promotion of magnesium absorption and of magnesium retention at a low dose, expected to have a good digestive tolerance, especially in the infant population.

The invention claimed is:

1. A method for the promotion of magnesium absorption and/or magnesium retention in an infant or child who was born preterm or with low-birth weight (LBW), the method comprising administering a composition comprising an oligosaccharide mixture to the infant or child, the oligosaccharide mixture containing
   at least one N-acetylated oligosaccharide selected from the group consisting of GalNAcα1,3Galβ1,4Glc; Galβ1,6GalNAcα1,3Galβ1,4Glc; Galβ1,4GlcNAcβ1,3Galβ1,4Glc; and Galβ1,3GlcNAcβ1,3Galβ1,4Glc,
   at least one sialylated oligosaccharide selected from the group consisting of NeuAcα2,3Galβ1,4Glc and NeuAcα2,6Galβ1,4Glc, and
   at least one neutral oligosaccharide selected from the group consisting of Galβ1,6Gal; Galβ1,6Galβ1,4Glc; Galβ1,6Galβ1,6Glc; Galβ1,3Galβ1,3Glc; Galβ1,3Galβ1,4Glc; Galβ1,6Galβ1,6Galβ1,4Glc; Galβ1,6Galβ1,3Galβ1,4Glc; Galβ1,3Galβ1,6Galβ1,4Glc; Galβ1,3Galβ1,3Galβ1,4Glc; Galβ1,4Galβ1,4Glc; Galβ1,4Galβ1,4Galβ1,4Glc; and Fucα1,2Galβ1,4Glc,
   the at least one neutral oligosaccharide is 10-50 wt. % of the total weight of the oligosaccharide mixture.

2. The method of claim 1, the composition further comprising at least one long chain polyunsaturated fatty acid (LC-PUFA).

3. The method of claim 1, the composition further comprising at least one probiotic.

4. The method of claim 1, wherein the oligosaccharide mixture is present in an amount of 0.5-50% with respect to the total weight of the composition.

5. The method of claim 1, wherein the at least one N-acetylated oligosaccharide is selected from the group consisting of Galβ1-4GlcNAcβ1-3Galβ1-4Glc and Galβ1-3GlcNAcβ1-3Galβ1-4Glc.

6. The method of claim 1, wherein the at least one sialylated oligosaccharide comprises NeuAcα2,3Galβ1,4Glc and NeuAcα2,6Galβ1,4Glc in a ratio between 5:1 and 1:2.

7. The method of claim 1, wherein the at least one neutral oligosaccharide is Fucα1,2-Galβ1,4Glc.

8. The method of claim 1, wherein the composition is selected from the group consisting of a preterm infant formula, a human milk fortifier, a starter infant formula, a follow-on formula, a baby food formula, an infant cereal formula, a growing-up milk, a medical food product for clinical nutrition and a supplement.

9. The method of claim 1, wherein the oligosaccharide mixture is 1-20% of the total weight of the composition.

\* \* \* \* \*